Figure 1:
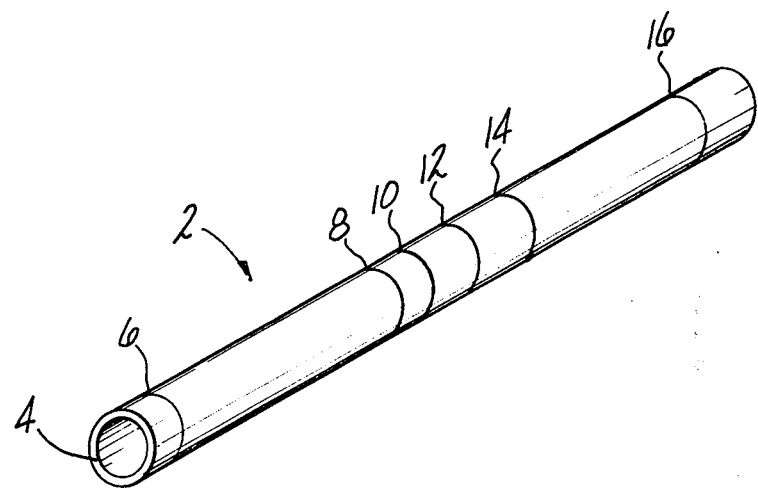

United States Patent [19]

Wardlaw et al.

[11] 4,141,654
[45] Feb. 27, 1979

[54] STANDARD FOR CALIBRATING AND/OR VERIFYING INSTRUMENT ACCURACY

[75] Inventors: Stephen C. Wardlaw, Branford; Robert A. Levine, Guilford, both of Conn.

[73] Assignee: James V. Massey, III, Trumbull, Conn.; a part interest

[21] Appl. No.: 799,178

[22] Filed: May 23, 1977

[51] Int. Cl.² .................. G02B 27/32; G01C 25/00
[52] U.S. Cl. ................................ 356/243; 73/1 J; 356/256
[58] Field of Search .............. 356/243, 256, 39, 42, 356/208, 197; 73/1 J, 1 H, 1 R; 33/125 A, 178 C; 128/26, DIG. 22

[56] References Cited

U.S. PATENT DOCUMENTS

| | | | |
|---|---|---|---|
| 3,291,693 | 12/1966 | Brown | 73/61 R |
| 3,371,524 | 3/1968 | Wloszek | 73/1 R |
| 3,488,498 | 1/1970 | Glowa et al. | 356/243 |
| 3,561,877 | 2/1971 | Nakada et al. | 356/158 |
| 3,885,415 | 5/1975 | Burns et al. | 356/243 |
| 3,918,908 | 11/1975 | Moyer et al. | 128/DIG. 2 |

*Primary Examiner*—John K. Corbin
*Assistant Examiner*—Wm. W. Punter
*Attorney, Agent, or Firm*—William W. Jones

[57] ABSTRACT

A device for use in checking and/or calibrating the accuracy with which a blood constituent concentration measuring instrument is operating. The device includes a capillary tube size member having annular bands marked on its outer surface. The bands are of predetermined axial extent and simulate centrifuged blood cell or other constituent layers. The axial dimension of each band is measured on the instrument which provides a visual indication of corresponding blood cell count. The blood cell count indicated by the instrument is then compared to the known blood count corresponding to the predetermined axial extent of the particular band measured. This device may be used to calibrate the instrument or determine the accuracy with which the instrument is operating.

1 Claim, 2 Drawing Figures

STANDARD FOR CALIBRATING AND/OR VERIFYING INSTRUMENT ACCURACY

This invention relates to a device for use in calibrating or checking the calibration of an instrument disclosed in copending patent application Ser. No. 788,509, filed Apr. 18, 1977 which, in turn, is used in taking blood count readings according to the technology and with the devices and methods disclosed in co-pending patent application Ser. No. 673,058 filed Apr. 2, 1976, now U.S. Pat. No. 4,027,660, issued June 7, 1977.

The general techniques for making blood count readings described in the above-identified patent applications utilize a capillary tube-insert combination which is used to elongate the axial extent of cell layers of the buffy coat of a centrifuged anticoagulated blood sample. The portion of the interior of the tube occupied by the buffy coat is a regular geometric form so that the length of the individual cell layers is generally proportional to the number of cells (cell count) in any discernable cell layer. The individual cell layers are rendered more visible by adding a colorant, preferably a fluorescent stain such as acridine orange, to the blood sample. The stain is absorbed to differing degrees by the different cell types in the buffy coat so that the different cell types therein appear in the tube as differently colored bands. Thus, in the centrifuged tube, the red cell layer appears red, the granulocyte layer portion of the buffy coat appears as an orange band, the mono-nuclear layer portion of the buffy coat appears as a green band, the platelet layer portion of the buffy coat appears as a pink band, and the plasma of the blood sample displays a yellow coloration.

The instrument used in conjunction with the capillary tube-insert combination to measure the blood cell counts includes a light source which is directed at the tube to fluoresce the stain to accentuate the differential colorations. The tube is mounted on a movable stage in the instrument and viewed with an optical system which includes a reference line for alignment with the interfaces of the adjacent cell layers. A manipulatable dial is used to move the stage so that the reference line will be aligned with successive cell layer interfaces. Movement of the stage is electrically measured and a readout is activated to provide a visible indication of the respective cell counts. The circuitry includes means for automatically converting the linear movement to cell count so that the readout provides a cell count without further conversion. The instrument may be pre-calibrated at the factory, but it is essential that the ultimate user have means for checking the preset calibration of the instrument so as to be in a position to easily verify the accuracy of the measurements. In the event that the instrument is found to be off standard, appropriate corrective action, such as recalibration, can be effected.

In order to ensure that the instrument is operating correctly, we have devised a standard indicating device which can be used by one who has merely been trained to operate the instrument, but is not necessarily familiar with the construction of the instrument, to check the accuracy with which the instrument is operating.

The device includes a capillary tube or an article simulating the same, which is provided with appropriately differentially colored bands corresponding to a centrifuged blood sample having known cell counts, i.e., a known hematocrit, a known granulocyte count, a known mono-nuclear count and a known platelet count. The bands are preferably painted on the exterior of the tube and correspond in color to the colors observed in an actual blood sample. Alternatively, the bands may be merely delineated by properly spaced lines painted or etched onto the tubular article. A printed reference card will be included with the standardized tube so as to inform the user of the cell counts which are preset on the standard. If the bands are painted on the tube, they may be painted on the inside or outside of the tube, and a fluorescent paint may be used. The etching may also be on the inside of the tube. Additionally, if desirable, the preset markings could be disposed on an insert which is positioned in the bore of the capillary tube.

An additional advantage in such a "standard" is that it could be varied to reflect changes in manufacturing tolerances of the capillary tube-insert combinations with which it is supplied. Changes in manufacturing tolerances between various batches could result in a difference in the number of cells per unit of axial dimension. This could be compensated for by including the described "standard" in each lot of said tubes, said "standard" allowing the reading instrument to be calibrated by the user.

Additionally, because of slightly different packing factors of layers resulting from the use of different intensities of centrifugation inherent in the use of different conventional blood centrifuges on the market, several lists of standard values corresponding to different centrifuging equipment can be used to calibrate the instrument for the particular centrifuge being used.

It is, therefore, an object of this invention to provide a device for determining whether a blood testing instrument is operating properly.

It is a further object of this invention to provide a device of the character described which is of capillary tube size and includes spaced indicia marked on the device to reproduce known blood sample constituent counts.

It is another object of this invention to provide a device of the character described wherein the indicia are produced by painting colored bands on the device.

Figure 2:
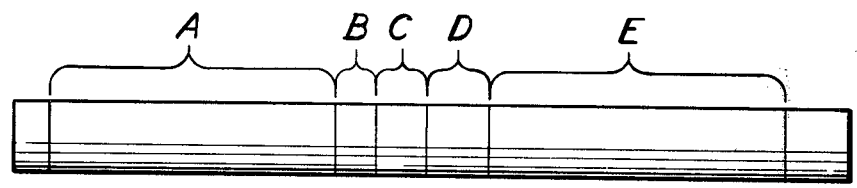

These and other objects and advantages of the invention will become more readily apparent from the following description of a preferred embodiment of the invention taken in conjunction with the accompanying drawings, in which:

FIG. 1 is a perspective view of a device formed in accordance with this invention; and FIG. 2 is a side elevational view of the device of FIG. 1.

Referring now to the drawings, there is shown a capillary tube 2 of about three inches in length. Adjacent to and spaced apart from one end 4 of the tube 2 there is a first circumferential mark 6 visible from the exterior of the tube 2. The first mark 6 denotes the boundary between the conventional clay or wax plug, which is inserted into the open end of a capillary tube when a blood sample is centrifuged therein, and the lower end of the red cell layer. Next there is visible from the exterior of the tube 4 a circumferential mark 8 which denotes the boundary between the red cell layer and the granulocyte layer. After the mark 8, longitudinally along the tube 2 there next is seen a circumferential mark 10 which denotes the boundary between the granulocytes and the mono-nuclear cells. The next circumferential mark 12 visible from the exterior of the tube 2 denotes the boundary between the mono-nuclear cells and the platelets, and the next circumferential mark 14 denotes the boundary between the platelets and the plasma. The last circumferential mark 16 denotes the upper boundary of the plasma.

The successive marks referred to above, form adjacent bands A, B, C, D, and E which correspond in longitudinal dimension to blood constituent layers, namely, red cells, granulocyte cells, mono-nuclear cells, platelets, and plasma, respectively.

The most important reference bands are B, C and D, since the red cell count, band A, is measured with a fixed scale on the exterior of the instrument, normally. The width of the bands (length measured longitudinally of the tube) formed on the tube may be any given value which will correspond to a known cell count measured in a standard tube-insert combination. For example, we have determined that a band width of 0.050 in. for the band B equals a granulocyte count of about 6,500, a band width of 0.015 in. for the band C equals a mono-nuclear cell count of about 3,150, and a band width of 0.100 in. for the band D equals a platelet count of about 424,000, all of which band widths and respective count values relate to an actual cell testing tube-insert combination wherein the tube bore is a constant 0.04683 in diameter and the insert has a cylindrical side wall of a constant 0.0438 diameter in the buffy coat cell packing zone with a contained blood volume of about 0.0065 ml. of anticoagulated blood.

As previously noted, the several bands can be formed by spaced circumferential lines scribed, painted, or otherwise formed on the exterior or interior of the tube bore, or the bands can be painted in different colors on the interior or exterior of the tube. Fluorescent paints can be used to provide the different colored bands. The bands can be painted the same colors as the actual cell bands assume in the testing apparatus, for example, if the actual testing apparatus uses acridine orange fluorescent stain, the bands B, C, and D can be painted orange, green and pink, respectively. The device is used by simply mounting it in the instrument to be checked, in the same manner as an actual blood-containing centrifuged tube, and by measuring the known bands on the instrument. The blood count readings given by the instrument can then be compared to the "correct" blood count readings represented by the known bands on the device and the accuracy of the instrument thus determined. Periodic accuracy checks are thus easily accomplished.

Since changes and variations of the disclosed embodiment of the invention may be made without departing from the inventive concept, it is not intended to limit the invention otherwise than as required by the appended claims.

What is claimed is:

1. A device for checking the accuracy with which a blood constituent concentration measuring instrument is operating, said device comprising:
    (a) a capillary tube size member; and
    (b) a plurality of differentially colored bands painted on said member with fluorescent paint, the boundaries of said bands defining a plurality of circumferentially extending lines visible from the outside of said member and spaced apart from each other axially of said member, said bands corresponding in thickness to the thickness of different physically elongated layers of centrifuged blood constituents having known concentrations in a centrifuged blood sample to give the appearance of an actual sample, whereby the thickness of said bands can be measured in the measuring instrument to check the accuracy of the instrument.

* * * * *